(12) United States Patent  (10) Patent No.: US 8,721,725 B2
Keller  (45) Date of Patent: May 13, 2014

(54) INTERVERTEBRAL PROSTHESIS WITH SELF-TAPPING FIXING PROJECTIONS

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 268 days.

(21) Appl. No.: 12/753,031

(22) Filed: Apr. 1, 2010

(65) Prior Publication Data

US 2010/0191334 A1    Jul. 29, 2010

Related U.S. Application Data

(63) Continuation of application No. 11/472,543, filed on Jun. 22, 2006, now abandoned.

(60) Provisional application No. 60/693,086, filed on Jun. 23, 2005.

(51) Int. Cl.
    *A61F 2/44*    (2006.01)

(52) U.S. Cl.
    USPC ........................................... 623/17.16

(58) Field of Classification Search
    USPC .......................................... 623/17.11–17.16
    See application file for complete search history.

(56) References Cited

U.S. PATENT DOCUMENTS

| 5,425,772 | A * | 6/1995 | Brantigan ................ 623/17.11 |
| 6,592,624 | B1 * | 7/2003 | Fraser et al. ............. 623/17.16 |
| 6,682,562 | B2 | 1/2004 | Viart et al. |
| 6,827,740 | B1 | 12/2004 | Michelson |
| 2003/0069640 | A1 | 4/2003 | Ferreira et al. |
| 2004/0002761 | A1 | 1/2004 | Rogers et al. |
| 2004/0117021 | A1 | 6/2004 | Biedermann et al. |
| 2005/0055029 | A1 | 3/2005 | Marik et al. |
| 2005/0075734 | A1 * | 4/2005 | Fulton et al. ............... 623/17.16 |
| 2005/0159746 | A1 * | 7/2005 | Grob et al. ..................... 606/61 |
| 2005/0159819 | A1 * | 7/2005 | McCormack et al. ..... 623/17.16 |
| 2006/0136059 | A1 | 6/2006 | Thramann et al. |
| 2006/0178746 | A1 * | 8/2006 | Bartish et al. .............. 623/17.13 |
| 2006/0217809 | A1 * | 9/2006 | Albert et al. ............... 623/17.11 |

FOREIGN PATENT DOCUMENTS

| DE | 3023353 | A1 | 4/1981 |
| EP | 1057462 | A1 | 5/1999 |
| EP | 1103237 | A2 | 5/2000 |
| EP | 1405615 | A1 | 8/2003 |
| FR | 2659226 | A1 | 9/1991 |
| FR | 2718635 | A1 | 10/1995 |

(Continued)

OTHER PUBLICATIONS

International Search Report dated Oct. 11, 2006, directed to a counterpart PCT Application No. PCT/EP2006/005910.

*Primary Examiner* — Jan Christopher Merene
*Assistant Examiner* — Steven Cotroneo
(74) *Attorney, Agent, or Firm* — Jonathan Spangler; Marjorie Jarvis

(57) ABSTRACT

An intervertebral prosthesis, in particular for the cervical spine, has two attachment plates connected in an articulated manner. The attachment surfaces of the attachment plates, which are configured for attachment to adjacent vertebral bodies have a base surface configured to bear on the surface of the vertebral bodies, and self-tapping fixing projections rising from the base surface. These fixing projections are formed by at least one pair of ribs which extend in opposite directions obliquely with respect to a predetermined implantation direction and whose side faces oriented more away from the implantation direction are steeper than their side faces oriented more in the implantation direction. The ribs can be toothed.

5 Claims, 2 Drawing Sheets

(56) References Cited

FOREIGN PATENT DOCUMENTS

| WO | WO-00/40179 A1 | 7/2000 |
| WO | WO-01/01893 A1 | 1/2001 |
| WO | WO-2004/080355 A1 | 9/2004 |
| WO | WO-2004/089259 A1 | 10/2004 |
| WO | WO-2005/007040 A1 | 1/2005 |

* cited by examiner

INTERVERTEBRAL PROSTHESIS WITH SELF-TAPPING FIXING PROJECTIONS

REFERENCE TO RELATED APPLICATION

This application is a continuation of U.S. application Ser. No. 11/472,543 filed Jun. 22, 2006, which claims the benefit under 35 U.S.C. §119(e) from U.S. provisional application Ser. No. 60/693,086, filed Jun. 23, 2005, the entire contents of which are hereby expressly incorporated by reference into this disclosure as if set forth fully therein.

FIELD AND BACKGROUND OF THE INVENTION

Intervertebral prostheses need to be fixed to the adjacent vertebral bodies in order to ensure that they do not shift from the position assigned to them. It is known to provide them with ribs or studs which are fitted into correspondingly shaped fixing recesses in the cover plates of the vertebral bodies (WO 01/01893, WO 2004/080355, DE-3023353, FR-A-2659226). Producing these requires deep working of the cover plates of the vertebral bodies, which entails considerable outlay in operating terms. Such working of the cover plates of the vertebral bodies is also undesirable, and in the area of the cervical spine often impossible, because it demands considerable distraction and presupposes a substantial thickness of the vertebral bodies.

Particularly for the cervical spine, prosthesis structures are therefore preferred which do not demand the formation of fixing recesses in the cover plates of the vertebral bodies. These prosthesis structures include prostheses in which the outer faces of the attachment plates have a transversely extending toothed arrangement covering more or less the whole surface area and with a sawtooth profile whose steep flanks are arranged ventrally (WO 2004/089259, FR-A-2718635). Although a displacement of the prosthesis in the ventral direction can normally be prevented by this means, cases nevertheless occur where, because of unusual anatomy or unsuitable surgical preparation, the intervertebral space opens out in such a pronounced wedge shape in the ventral direction that the prosthesis cannot be securely held in place by the toothing alone. This is because the toothing does not penetrate into the bone surface. It is not intended to do so, in order not to extensively damage and thus weaken the cortical bone. Instead, it is intended to bear on the bone surface, which in normal circumstances is adequate to ensure fixation, since it then also secures itself on surface irregularities.

Intervertebral prostheses with self-tapping fixing projections are also known (EP-A-1057462, EP-A-1103237). The outer face of the attachment plates of the prosthesis forms an attachment surface for connection to the vertebral body. It comprises a base surface which is intended to bear on the bone surface, and fixing projections which rise from the base surface and which are so sharp that, under the natural loading of the articulation, and by means of the force of the ligaments and the transmitted weight, they penetrate into the bone surface as soon as the distraction of the vertebral bodies is cancelled. However, the known prostheses of this kind require considerable distraction to ensure that they are not impeded by the fixing projections when fitted into place. This can in some cases be tolerated in the region of the lumbar spine and thoracic spine, but not in the region of the cervical spine. If they were to be pressed in without sufficient distraction, the fixing projections would carve out channels in the cover plates of the vertebral bodies, and they could then slide out again through these channels, in addition to which the channels are undesirable because of the loss of strength they entail.

SUMMARY OF THE INVENTION

The problem addressed by the invention is therefore that of making available an intervertebral prosthesis with self-tapping fixing projections which can be introduced into a secure fixing position even with just slight distraction of the vertebral bodies, without excessive damage to the cover plates of the vertebral bodies in the area lying ventrally of their fixing position.

The solution according to the invention lies in the features disclosed herein. Accordingly, the fixing projections are formed by at least one pair of ribs extending in opposite directions obliquely with respect to the implantation direction. The implantation direction is generally the AP direction (AP=antero-posterior). The ribs are expediently arranged symmetrically with respect to the median plane (central sagittal plane). As a consequence of their oblique arrangement, the ribs have one side face oriented more and one side face oriented less away from the implantation direction. The side face oriented more away from the implantation direction, and generally in the ventral direction, is steep and preferably approximately perpendicular to the base surface, in order to generate considerable resistance against a forwardly directed movement of the prosthesis and to secure it by this means in the intervertebral space. The other side face, which is oriented less away from the implantation direction and generally dorsally, is gently inclined in order to reduce the resistance during insertion of the prosthesis and to protect the bone surface across which the ribs slide. By virtue of its lesser inclination, it forms a slide-on surface.

Any irregularities in the bone surface, which would be planed away if the leading face of the ribs during implantation was steep and sharp, can slide across this surface onto the rib without damage or with only minimal damage. Measured in a plane extending parallel to the implantation direction, it should enclose an angle of less than 45° with the base surface. It is assumed here that the base surface extends approximately parallel to the main directions of the attachment plate. The slide-on surface can be smooth in order to offer little resistance and in order to cause the least possible damage to the bone surface. However, an embodiment is also advantageous in which the slide-on surface is roughened and for example provided with small teeth which, after implantation, connect intimately with the bone surface in order to obtain an additional fixing effect.

The rib can have a substantially uniform and constant profile. This profile should be sharp enough to ensure that the rib can penetrate into the bone surface, under the loading of the articulation, after the distraction has been cancelled. The slide-on surface is then formed by its more dorsally oriented side face.

An embodiment is preferred in which the rib is interrupted a plurality of times in order to form a series of pointed or sharp teeth. This reduces the size of the cross-sectional surface area of the rib (in a sectional plane extending parallel to the surface extent of the prosthesis), which determines the resistance to penetration into the bone surface. This rib formed by teeth therefore penetrates more easily and more deeply into the bone surface than a continuous rib with a similar profile. If, according to a further feature of the invention, the interruptions extend transverse to the AP direction, they form additional surfaces which counteract a movement of the prosthesis in the ventral direction. These surfaces too should therefore be steep. The interruptions can be produced more easily if they extend parallel in all the ribs.

The teeth, which form the ribs in this embodiment, have four limit surfaces. A first limit surface is formed by the more ventrally oriented side face of the rib extending obliquely with respect to the sagittal direction. A second limit surface is that of the first opposite side face of the rib which generally extends parallel to the first one and is oriented more in the implantation direction. A third and a fourth limit surface are formed by the interruptions between the teeth. The third surface is oriented away from the implantation direction and is steep. The fourth one is oriented in the implantation direction and is less steep. The third and fourth surfaces give the teeth a sawtooth profile. Both the second surface and the fourth surface act as a slide-on surface. The second surface acting as slide-on surface can also be inclined relative to the prosthesis plane, but the fourth surface is in most cases the more important one for the slide-on resistance.

In another embodiment of the invention, the interruptions extend parallel to the implantation direction. The size of the edge acting with a scraping effect on the bone surface during implantation is thereby reduced. In this case, only the side faces of the rib extending obliquely with respect to the implantation direction from the resistance against the movement of the prosthesis in the ventral direction and from the slide-on surface on the dorsal face.

Where the word steep is used in the present context, this signifies an angle to the base surface of almost 90°. It is expediently greater than 70°, this angle being measured either in a plane lying perpendicular to the measured flank and to the base surface or preferably in a sagittal plane. It can be in excess of 90° (undercut).

The self-tapping property of the ribs is mainly described by their cross-sectional surface parallel to the base surface. To ensure that the articulation forces suffice to press the ribs sufficiently into the bone surface, these take up only a small proportion of the total attachment surface. The surface proportion on the attachment surface which they take up when fully embedded in the bone, which is their total surface proportion on the attachment surface, should not be greater than a fifth, preferably not greater than a tenth. Since it is not necessary for them to have pressed completely into the bone directly after the operation, it is expedient if their cross-sectional surface area at mid-height parallel to the base surface is not greater than one tenth, preferably one twentieth of the attachment surface. They should be sharp or pointed to ensure that, even in the case of unusually small articulation forces, they press slightly into the bone immediately after the operation. The words sharp or pointed signify that the edge angle or point angle is not above 50°. In the case of a point having different point angles in different point planes, the smallest point angle is critical.

The end plates of the vertebral bodies offer resistance to the pressing-in of the ribs or of the teeth forming the latter, said resistance being greater, the more dense the end plates. Since the density in the central area is less than in the outer area, the ribs should be arranged principally in the inner area of the attachment surfaces. To be more exact, in at least half of the surface taken up by them, they should be at a distance of more than one sixth of the AP dimension of the attachment surface from the nearest boundary thereof. In particular, the dorso-lateral areas of the attachment surface should be free of ribs, so that the base surface there can transfer force onto compact, undamaged bone substance.

The ribs are preferably arranged in a V-shape with an interspace opening out toward the front. At least the ribs of one rib pair approach one another in the dorsal direction. A reverse configuration is also possible. However, it has proven expedient if the ribs enclose between them, on their ventral face, a continuous block of bone substance and prevent this from moving in the ventral direction. Several parallel ribs can be arranged on each side of the axis of symmetry. In general, however, one rib on each side is sufficient.

The height of the ribs above the base surface should be sufficient for secure engagement in the bone substance. It should generally not be less than 0.5 mm. Their height is limited by the aim of minimizing the distraction during implantation and the scraping off of the cover plates of the vertebral bodies by the fixing projections. It should generally not exceed 2 mm (preferably 1.6 mm) or one eighth (preferably one tenth) of the AP dimension of the attachment surface. A height of 0.7 to 1.5 mm has proven useful for cervical prostheses. The height is to be measured above the base surface, i.e. that surface surrounding the ribs which is expected to bear on the bone. If this surface has a roughness, for example a porous coating or an arrangement of rows of teeth substantially covering the whole surface area, with bone substance intended to grow into the gaps between the teeth over the course of time, the surface area of this roughness is a critical factor.

The angle that the ribs enclose with the implantation direction does not need to be large. The angle formed by the more ventrally oriented side faces of the ribs is preferably smaller than 60° and more preferably smaller than 30°. Angles of between about 10 and 20° have proven particularly expedient.

The permanent fit of the prosthesis is compromised particularly if the intervertebral space opens out in a pronounced wedge shape in the ventral direction. Since in this case the connection between the attachment plates of the prosthesis and the end plates of the vertebral bodies is more secure in the dorsal area than in the ventral area, the invention proposes that the ribs are active at least also in the dorsal area of the attachment surfaces. For this purpose, at least one rib pair should reach at least to one fifth of the AP dimension of the attachment surface at the dorsal boundary thereof, preferably at least to one tenth of the AP dimension.

BRIEF DESCRIPTION OF THE DRAWINGS

The invention is explained in more detail below with reference to the drawing which depicts advantageous illustrative embodiments and in which.

DETAILED DESCRIPTION OF THE INVENTION

Figure 1:
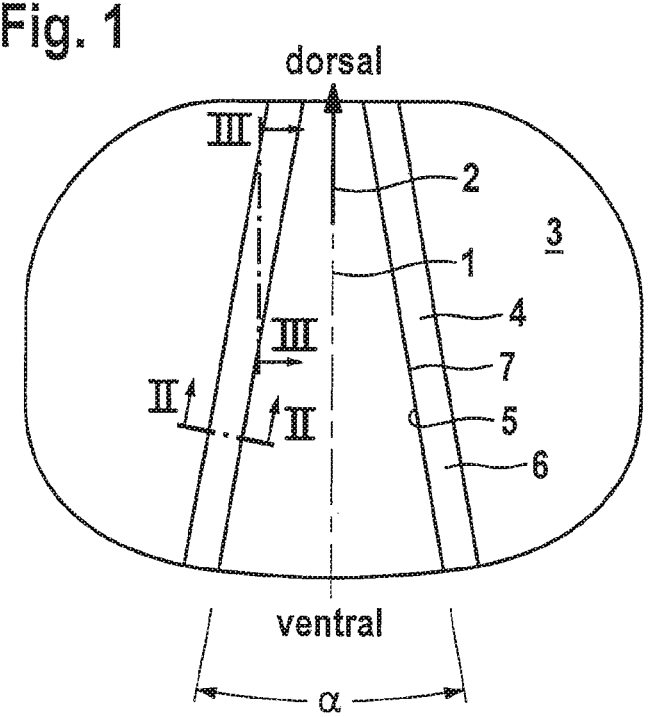
FIG. 1 shows a plan view of an attachment plate.

FIG. 1 shows the view of the attachment surface of an attachment plate of the prosthesis which is symmetrical with respect to the median plane 1. Its adaptation to the shape of the intervertebral space means that it has a predetermined ventral face and dorsal face. The implantation direction is also predetermined and, in the examples shown, is the direction 2 leading from ventral to dorsal.

The attachment surface includes a base surface 3 which is intended to bear on the bone as far as possible across its entire surface area and can be provided with a surface structure permitting an intimate connection by means of bone tissue growing in pores or other recesses. The base surface surrounds two ribs 4 which are arranged symmetrically with respect to the median plane 1 and enclose an angle alpha of approximately 20°. Their more ventrally oriented side face 5 is steep, namely approximately 90° to the base surface 3, and the more dorsally oriented side face 6 running parallel thereto is inclined obliquely at an angle of approximately 45° to the base surface 3 in a sectional plane (FIG. 2) extending perpendicular to the rib. In a cross section extending parallel to the implantation direction (FIG. 3), the angle appears much flatter. However, it is arranged in such a way that, during the implantation movement, it slides gently onto the bone surface or cartilage surface of the vertebral body cover plate assigned to it. This even applies when the vertebral bodies involved have not first been distracted to a spacing greater than the thickness of the prosthesis. It is for this reason that it is designated as a slide-on surface. Since the two side faces 5 and 6 enclose an angle of approximately 45° (or preferably even less) with one another, they form a sharp cutting edge 7 at the head of the rib.

When the force of the ligaments connecting the vertebral bodies, and the load to be taken up by the spinal column, move the vertebral bodies concerned toward one another after the implantation, the rib penetrates completely or partially into the bone tissue and thereby anchors the prosthesis in the desired position. It is not necessary for it to sink to its full height into the bone immediately after the operation; however, one seeks to ensure that, within a short period of time after the operation, the base surface 3 bears across a large area on the bone surface. This is achieved, on the one hand, by the sharpness of the rib and, on the other hand, by its small surface proportion of the total surface area of the attachment surface. This surface proportion is minimal at the head of the rib and increases, as far as its mid height, to approximately 5% of the size of the attachment surface. It is expected that the rib will sink at least approximately to this depth into the bone shortly after the operation. Its surface proportion measured at its foot is approximately twice as great.

The fixing effect of the ribs 3 is based on their interaction with the bone substance enclosed between them. The prosthesis could escape from the intervertebral space only if its more ventrally oriented side faces 5 were to compress this bone substance between themselves. It offers such strong resistance to this deformation that the implant is sufficiently secured in its position by this means. This also applies directly after the operation, because the inclined shape of the slide-on surface 6 has the effect that the bone substance or cartilage substance directly adjacent to each rib on the ventral face or inside face has not been milled off or scraped off by the rib 4 during the implantation, or has been so only to a slight extent, and is therefore still available for securing the prosthesis.

Figure 4:
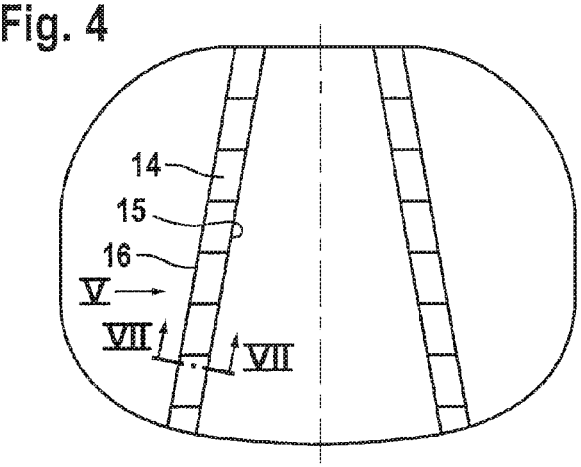
FIG. 4 shows a plan view of a second embodiment.

In the embodiment according to FIG. 4, the ribs 14, which are delimited by side faces 15, 16, are toothed transversely. The teeth 17 are sawtooth-shaped with a steep ventral face 18, and a gently inclined dorsal face 19 as slide-on surface. The tooth profile expediently extends at 90° to the median plane 1, so that the teeth of all the ribs can be produced by uniform planing. However, if this aspect is not critical, they can be chosen to have a different direction.

For example, a profile extending parallel to the implantation direction 2 can be used in which (viewed in the implantation direction) gaps are present between the teeth. This has the advantage that the implantation resistance is greatly reduced. It is true that this profile cannot avoid the teeth to some extent scraping onto the bone surface during the implantation; however, they do not drive the scraped-off or displaced substance ahead of them and instead leave it in the gaps of the teeth. When the teeth have reached their final position, the substance is not located on their dorsal side but instead in the immediate proximity of their ventral side. It is therefore able to promote the postoperative anchoring of the teeth.

Figure 2:
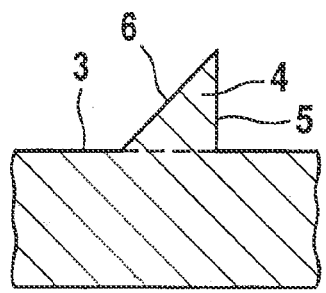
FIG. 2 shows a cross section along the line II-II in FIG. 1.
Figure 3:
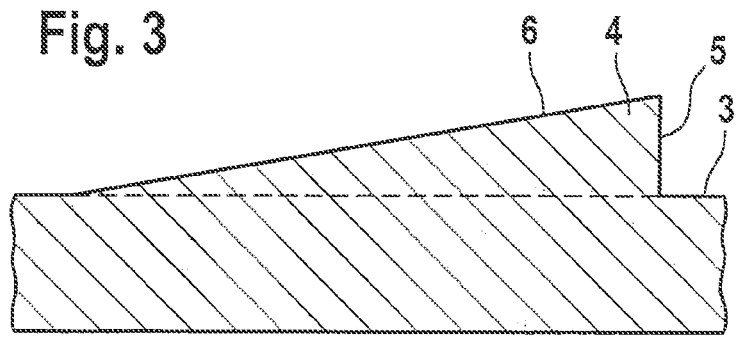
FIG. 3 shows a cross section along the line III-III in FIG. 1.
Figure 7:
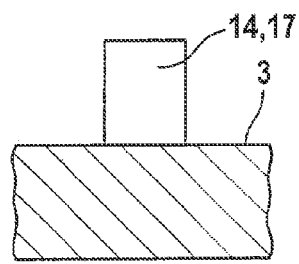
FIG. 7 shows a cross section along line VII-VII in FIG. 4, and
FIGS. 8 and 9 show plan views of other rib arrangements.

In the embodiment according to FIG. 4, the rib profile (viewed in the longitudinal direction of the ribs) can also be configured as shown in FIG. 2, i.e. gently sloping down on the side face 16. The slide-on surface of the rib 14 is then formed not only by the dorsal face 19 of each individual tooth 17, but also by the side face 16 of the rib 14. However, a rib profile as shown in FIG. 7 can also be chosen in which the side face 16 is just as steep as the side face 15. In this case, the dorsal faces 19 of the teeth 17 alone form the slide-on surface. It is also possible to choose intermediate stages in which the side face 16 is inclined at a relatively steep angle, which however gives a substantially flatter slide-on angle in the cross section according to FIG. 3 which is critical for the implantation procedure.

Figure 5:
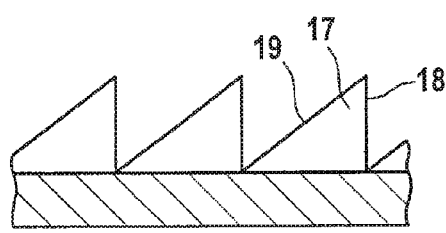
FIG. 5 shows a view according to arrow V in FIG. 4.
Figure 6:
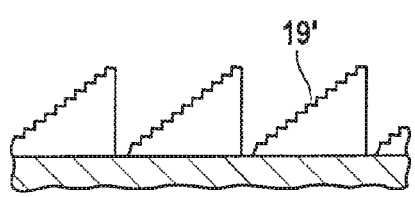
FIG. 6 shows the same view of a modified embodiment.

If the dorsal face 19 of the teeth 17 is smooth (FIG. 5), this has a favorable effect on protecting the bone surface during implantation. However, it may also be advantageous for it to be roughened in order to provide an additional anchoring possibility after implantation. This variant is shown in FIG. 6, which shows a fine toothing on the surfaces 19'.

It is important that the implant is well anchored in the dorsal area of the intervertebral space, because there is a possibility of the attachment plates lifting from the vertebral body surfaces in the ventral area if, just after implantation, when the attachment plates have not yet become joined to the bone surface, a strong lordotic flexion of the spinal column happens to take place. It is therefore expedient if the ribs 4, 14 are guided approximately to the dorsal edge of the attachment surface. On the other hand, it would be desirable to use the edge areas of the end plates of the vertebral bodies for transmitting load forces from the bone to the prosthesis, because their greater density means they are well-suited for taking up forces. The invention satisfies both objectives if the ribs, in at least half of the surface area taken up by them, are at a distance of more than a sixth of the AP dimension of the attachment surface from the boundary thereof. The AP dimension is the dimension in the antero-posterior direction.

Figure 8:
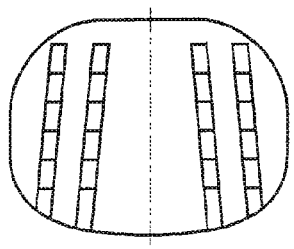
Figure 9:
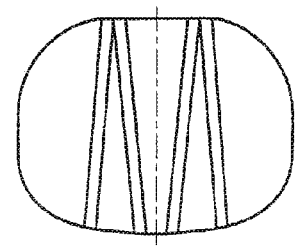

The arrangement according to the invention does not have to be limited to one pair of ribs. Instead, as is illustrated in FIGS. 8 and 9, several pairs can be present. In the examples shown, they are arranged such that they enclose a V-shaped interspace opening out in the ventral direction. This interspace can also open out dorsally, however, as is the case in the embodiment according to FIG. 9 between the two central ribs.

What is claimed is:

1. A method of securing an intervertebral prosthesis between adjacent vertebral bodies, comprising the steps of:
 preparing a disc space for receiving the intervertebral prosthesis;
 inserting the intervertebral prosthesis into the prepared disc space under slight distraction, the intervertebral prosthesis comprising two attachment plates connected in an articulating manner, the attachment plates comprising a base surface and cutting teeth, the base surface configured with serrated ridges for attachment to an endplate of an adjacent vertebral body, the cutting teeth configured to be self-tapping and to penetrate into the endplate of the adjacent vertebral body without forming a fixation channel in the endplate to receive the cutting teeth, each of the cutting teeth extending from the base surface and defined by an inclined posterior-facing surface, a steep anterior-facing surface, a medial-facing side surface, and a lateral-facing side surface, wherein the cutting teeth are arranged in at least two non-connected rows arranged with an interspace opening located between a convergence of the rows, the rows arranged symmetrically about a median plane in an anterior to posterior direction wherein the at least two rows converge in the posterior direction and open outward in the anterior direction, and the steep anterior-facing surface extends at 90° to the medial plane, wherein the inclined posterior-facing surface is a slide-on surface that gently distracts the endplates during insertion; and releasing the distraction force which presses the cutting teeth into the vertebral endplates; wherein the cutting teeth connect intimately with the vertebral endplates to provide primary fixation of the intervertebral prosthesis.

2. The method of claim 1, wherein the inclined posterior-facing surface of the cutting teeth is configured with an angle of inclination of less than approximately 45° to reduce the resistance during insertion of the intervertebral prosthesis and to preserve the integrity of the vertebral endplates during insertion.

3. The method of claim 1, wherein the steep-anterior facing surface is configured substantially perpendicular to the base surface to provide resistance against forward displacement of the intervertebral prosthesis after insertion.

4. The method of claim 1, wherein the arrangement of the at least two rows of cutting teeth forms a wedge of bone substance enclosed between the at least two rows to provide resistance against forward displacement of the intervertebral prosthesis after insertion.

5. The method of claim 1, wherein the base surface is substantially covered with a porous coating to promote bone tissue ingrowth to the attachment plate and to provide secondary fixation of the intervertebral prosthesis.

* * * * *